United States Patent [19]

Fenton

[11] Patent Number: 5,429,626
[45] Date of Patent: Jul. 4, 1995

[54] OSTOMY POUCH MOUNTING ARRANGEMENT

[76] Inventor: Leonard Fenton, 24761 Maidstone La., Beachwood, Ohio 44122

[21] Appl. No.: 209,304

[22] Filed: Mar. 14, 1994

[51] Int. Cl.⁶ .............................................. A61F 5/44
[52] U.S. Cl. ................................................... 604/339
[58] Field of Search ................................ 604/332–345

[56] References Cited

U.S. PATENT DOCUMENTS

| | | | |
|---|---|---|---|
| 4,834,731 | 5/1989 | Nowak et al. | 604/339 |
| 4,973,323 | 11/1990 | Kaczmarek et al. | 604/338 |
| 5,004,464 | 4/1991 | Leise, Jr. | 604/338 |
| 5,015,244 | 5/1991 | Cross | 604/344 |
| 5,330,454 | 7/1994 | Klinger et al. | 604/338 |

Primary Examiner—Jerome L. Kruter

[57] ABSTRACT

An ostomy appliance having a mounting member adapted to be secured to the periostomal skin surfaces of an ostomate is disclosed. The appliance includes a relatively rigid mounting plate having a centrally located aperture therethrough. The mounting plate defines a flat, annular flange portion radially extending from the aperture. An adhesive skin barrier is provided on a proximal side of the mounting member and defines a stoma-receiving opening. An adhesive web is provided on a proximal face of the flange to secure the plate to the ostomate. An ostomy pouch having a stoma inlet portal therein is adhesively secured to the distal face of the flange. The adhesive used allows repeated release and reattachment of the ostomy pouch to the mounting plate, while providing the requisite sealing and adhesion. This capability allows reuse of the pouch following cleaning, and avoidance of disposal problems, while assuring a secure seal.

12 Claims, 3 Drawing Sheets

5,429,626

OSTOMY POUCH MOUNTING ARRANGEMENT

BACKGROUND OF THE INVENTION

This invention relates to ostomy drainage receptacles and, more particularly, to an ostomy appliance having a mounting member secured to the periostomal skin surfaces of an ostomate to which an ostomy pouch is releasably attached. Ostomy appliances are either unitized assemblies which are attached to the body and removed for emptying or disposal, or are two-piece units which include a mounting member which is secured to the body by a mounting member such as a belt and/or adhesive and an ostomy pouch releasably attached to the mounting member. The latter arrangements provide convenience, economy, and comfort, since (a) it is relatively easy to replace merely the bag portion of the assembly, (b) a supply of bags may be purchased at a lesser cost, and (c) replacement of the bag portion of the assembly does not involve repeated peeling of the mounting adhesive from the skin. It should be appreciated that such repeated adhesive peelings may tend to ulcerate the skin surrounding the stoma.

Although the advantages of two-piece appliance assemblies have been recognized by the prior art, one problem associated with the practices of the prior art is the manner in which the bag or pouch is detachably secured to the mounting member. Some prior art assemblies, such as that shown in U.S. Pat. No. 4,834,731, provide a mechanical tongue-and-groove type interlock between the bag and the mounting member. Although this arrangement securely retains the bag on the mounting member, the force required to unlock the assembly may tend to peel the mounting member from the skin. More significant, however, is the fact that the interlock tends to retain contaminants and is difficult to clean. Furthermore, the assembly is comparatively thick and does not provide a low profile, particularly in those arrangements wherein the mounting member provides a flat surface to the periostomal skin area.

In another prior art ostomy assembly, disclosed in U.S. Pat. No. 5,015,244, the assembly is in two parts, and these are releasably attached by an adhesive. This assembly provides the benefit of fewer changes of the skin-attaching portion, but the bag is not reusable, and the adhesive on each bag portion is not reusable. This patent relies at least partially upon rapid biodegradability of the bag in addressing the problem of soiled bags.

SUMMARY OF THE INVENTION

The present invention provides a two-piece ostomy appliance which includes a mounting member adapted to be adhered to the periostomal skin surfaces of an ostomate and an ostomy pouch releasably attached and re-attachable to the mounting member. The mounting member comprises a relatively rigid or semi-flexible mounting plate having a centrally located stoma-receiving opening therethrough. The mounting plate includes a central portion and a flat annular portion radially extending from the central portion. An adhesive skin barrier is provided on a proximal face of the central portion and substantially covering the central portion to surround the stoma-receiving opening. An adhesive web is provided on the proximal face of the flat annular portion securely bonded to the proximal face of the flat annular portion and adapted to adhesively secure the plate to the periostomal skin surfaces of the ostomate. Preferably the adhesive web is a breathable, microporous material which will allow passage of water vapor from the skin, thereby allowing the skin to breathe. The adhesive used on the adhesive web means is preferably hypoallergenic, to avoid irritation of the ostomate's skin.

The distal side of the mounting plate includes a flat, annular flange portion, providing a base for releasably attaching an ostomy pouch, and providing means for properly aligning the ostomy pouch to the mounting plate adhesively attached to the ostomate.

The appliance further includes the ostomy pouch, which is formed of a plastic film, and which has a central stoma opening therein. The stoma opening or inlet portal is defined by a mounting ring having a circular opening therethrough which is provided with an annular band of pressure-sensitive adhesive to removably adhere the pouch to the distal face of the mounting plate. The preferred adhesive used to adhere the pouch allows the pouch to be released from its attachment to the mounting member, and to be re-attached to the mounting following cleaning of the pouch. The distal face of the mounting plate is most preferably composed on an ethylene vinyl acetate (EVA) copolymer having approximately 18% vinyl acetate and a melt index of 8.0 degrees per minute. The most preferred EVA is EL-VAX ®, a product of E. I. Du Pont de Nemours & Co., Inc. The adhesive chosen is a rubber based, pressure sensitive adhesive having high tack and high peel adhesion. The most preferred adhesive is Morstik ® 109, manufactured by Morton International, Inc., Chicago, Ill. It has been discovered that the combination of the preferred EVA copolymer and the preferred pressure-sensitive adhesive provide unexpectedly good results in the present invention, allowing the ostomy pouch to be cleaned and repeatedly reused with little or no loss in the strength of the adhesion of the bag to the mounting plate after repetitive reattachments, thus avoiding the problem of disposal of soiled bags.

To aid in the positioning and retention of the bag on the mounting member, the mounting plate is provided with an annular curb surrounding the stoma-receiving opening on its distal side. The annular curb has an outside diameter which is slightly less than the inner diameter of the circular stoma opening in the mounting ring so that the curb is positioned within the circular opening. The curb is substantially coplanar with a distal face of the mounting ring so that the entire assembly provides a relatively flat and less bulky arrangement.

The mounting ring on the bag is provided with diametrically opposed ears which may be employed to cooperate with a mounting belt worn by the ostomate. The mounting plate likewise may be provided with diametrically opposed tabs so that the user may grasp one of the tabs on the mounting plate and one of the ears on the mounting ring to separate the mounting ring from the mounting plate when the bag is to be replaced.

DETAILED DESCRIPTION OF THE INVENTION

Figure 1:
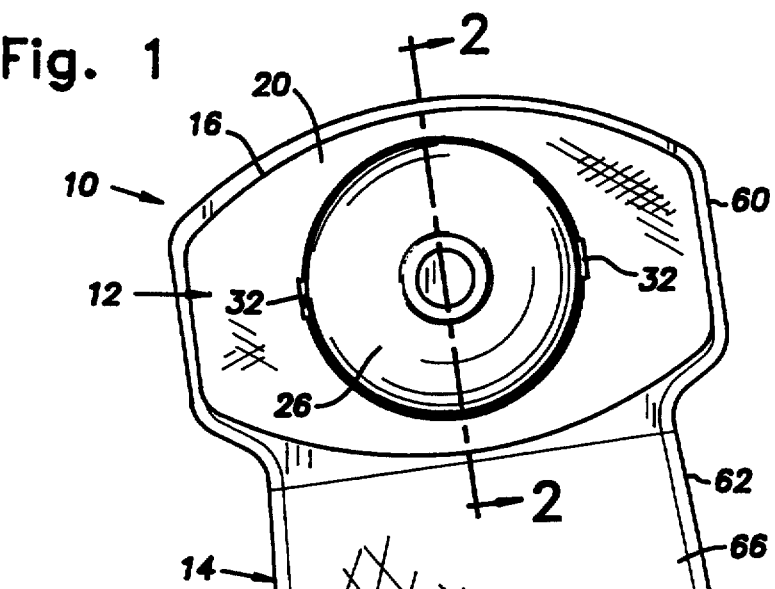
FIG. 1 is a proximal elevational view of an ostomy appliance according to this invention.
Figure 2:
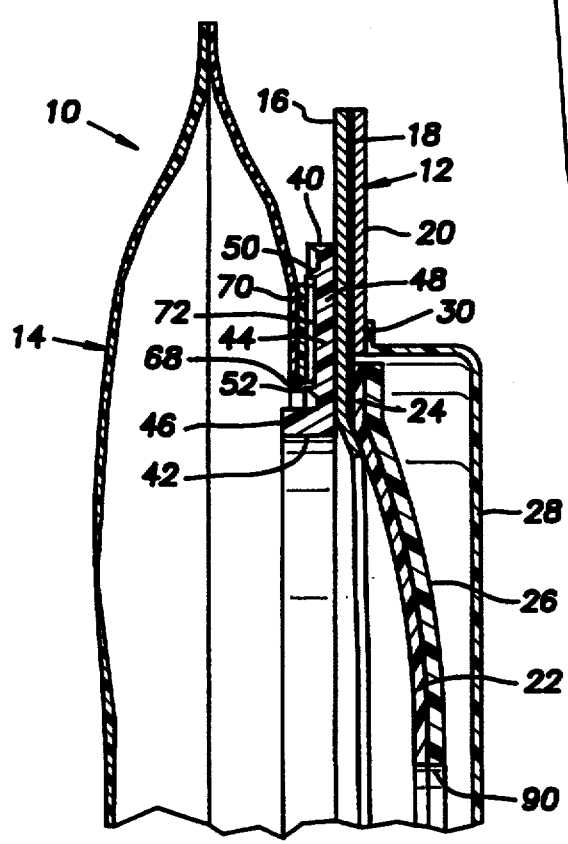
FIG. 2 is a cross-sectional view, the plane of the section being indicated by the line 2—2 in FIG. 1.
Figure 5:
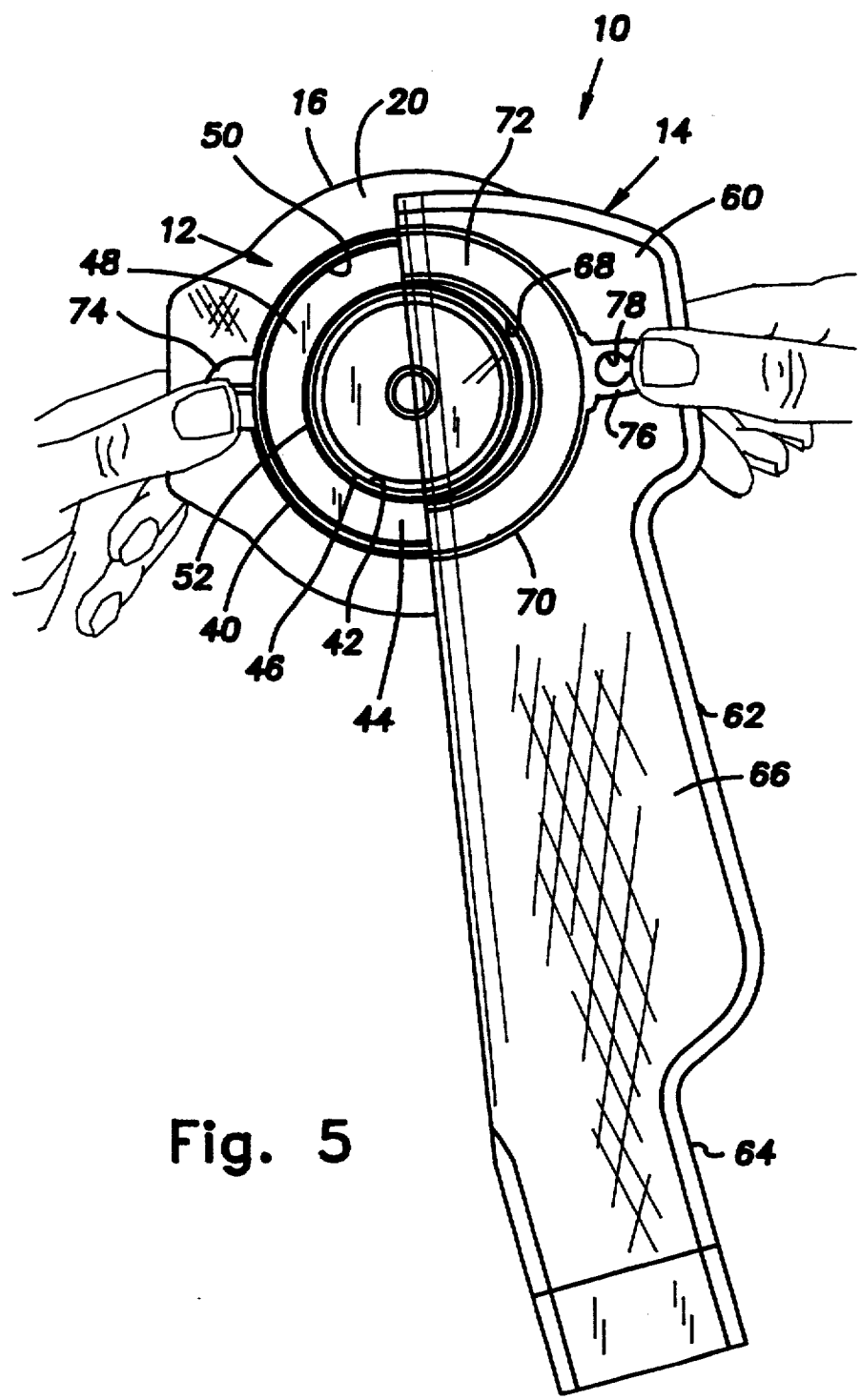
FIG. 5 is a proximal elevational view of the appliance illustrated in FIGS. 1 and 2, illustrating the manner in which the bag is applied to or removed from the mounting member.

Referring now to FIGS. 1, 2, and 5, there is illustrated an ostomy appliance assembly 10 according to a preferred aspect of this invention. The assembly 10 includes a mounting plate member 12 and an ostomy pouch 14. The mounting plate 12 is adapted to adhere to and be worn by the ostomate, and includes a web portion 16 having an adhesive coating 18 on its proximal surface. The web portion 16 covered by the adhesive coating 18 constitutes an adhesive web. The coating 18 is covered by a release liner 20. It may be noted that the web portion 16 provides a large oval-shaped adhesive area for secure adhesion to the skin, and is preferably composed of a breathable material. Adhesive coating 18 is preferably a hypo-allergenic adhesive.

An important innovation in the development of ostomy appliances is the provision of a convex pressure surface for the periostomal area to ensure that the stoma will adequately project into the drainage bag. Such a pressure surface is best illustrated in FIG. 2, and comprises a convex disc 22. The disc 22 may be molded from a stiffly flexible plastic, such as polyethylene or similar material. Preferably, disc 22 is molded from a copolymer of ethylene and vinyl acetate (EVA), wherein the vinyl acetate is present in the range of 9 to 40%, and the melt index of the copolymer is in the range of 0.3 to 50 degrees per minute (deg/min) by ASTM D 1238. More preferably, the copolymer has a vinyl acetate content in, the range of 15 to 20%, and a melt index in the range of 5 to 15 deg/min. Most preferably, the EVA copolymer is "Elvax ®" 450, produced by E. I. Du Pont de Nemours, Inc., Wilmington, Del., which has a vinyl acetate content of about 18% and a melt index of about 8.0 deg/min.

The convex disk 22 includes a flat, annular rim portion 24 which is securely bonded to the web 16 by ultrasonic techniques or permanent adhesives.

The proximal face of the disc 22 is covered with a layer of an adhesive skin barrier 26 which is pliable, and which has both dry and wet tack. Suitable materials are Karaya-glycerine formulations or mixtures of polyacrylamide resins and other polyols and mixtures of elastomers and hydrocolloids. Disc 22 includes a centrally located port 90, located so as to be positioned concentrically with a stoma inlet portal 68 of the ostomy pouch 14, and cooperating with the skin barrier 26 to form a stoma-receiving opening through the mounting plate 12 into the ostomy bag 14. Prior to use, the skin barrier 26 may be protected by a transparent plastic cup 28 which has a seating flange 30. The seating flange 30 is retained by exposed adhesive areas 32 (FIG. 1) of the adhesive layer 18 provided by cutout tab portions of the release liner 20.

The distal face of the web 16 carries a relatively rigid plastic mounting plate 40 which is securely bonded to the web 16 by permanent adhesives or suitable ultrasonic sealing techniques. The mounting plate 40 has a centrally located aperture 42 and a flat, annular flange portion 44 which radially extends from the aperture 42. The aperture 42 is defined by an annular curb 46 which projects axially from the flange portion 44. The flange portion 44 includes ,an annular seat 48 defined by concentric fences 50 and 52.

The mounting plate 40 is made of an EVA copolymer like that described above for the disc 22. The preferred EVA has a vinyl acetate content of 15 to 30% by weight TGA. The most preferred EVA is ELVAX ® 450, which has a vinyl acetate content of 18% by weight TGA and a melt index of 8.0 deg/min. This most preferred material is preferably the same as the most preferred material for disc 22.

The assembly 10 further includes the ostomy bag or pouch 14. The bag 14 is formed by sealing flexible plastic sheets of material together at their peripheries, and includes a relatively wide, bulbous upper portion 60, an intermediate drainage collection portion 62, and a relatively narrow drainage spout portion 64. The upper portion 60 accommodates protruding stomas. The spout portion 64 may be closed by a suitable clip or fastening device (not shown), which may be released for periodic discharge of bag contents without removing the bag from the mounting member. The proximal surface of the bag may be covered by a cloth-like, porous material 66 for the comfort of the wearer.

The flexible plastic sheets of the pouch are preferably formed of a multilayer extruded barrier film, having properties of softness and strength, and forming a barrier to passage of water and odors. Preferably, the material has two outer layers which provide softness and flexibility, and an inner layer which is impermeable to gases and water, and these layers are formed by a coextrusion process. The preferred barrier film has the two outer layers comprised of a copolymer of ethylene vinyl acetate, and an inner layer comprised of a vinylidene polymer plastic. The vinylidene polymer plastic is formed from a 1,1-dichloroethene monomer. Two barrier film materials are particularly preferred for use as the barrier film of the bag in the present invention. The first is CRYOVAC MF TM film, available from CRYOVAC, Inc., a division of W. R. Grace & Co., Duncan, S.C. The second preferred barrier film is DOW Saranex ® clear coextruded barrier film, available from DOW Chemical Company, Midland, Mich.

The ostomy pouch includes an opening 68 which is surrounded by a plastic mounting ring 70 having its proximal surface coated with a pressure-sensitive adhesive 72. The pressure sensitive adhesive should be a rubber based synthetic, and has high tack and high peel adhesion. The preferred pressure sensitive adhesive is a proprietary formulation based on a formulated styrene-butadiene rubber solution, having a high tack and a high peel adhesion and is capable of forming destructible bonds. The most preferred such adhesive is Morstik ® 109, manufactured by Morton International, Inc., 100 North Riverside Plaza, Chicago, Ill. Typical functional properties for a 1 mil layer of the preferred adhesive coated on a 2 mil polyester film, as provided by the manufacturer, are as follows:

| | |
|---|---|
| 180° Peel Adhesion (PSTC-1) 30 min. dwell | 5.6 (C)[1] piw |
| Polyken Tack (ASTM D-2979) | 1000 grams |
| Loop Tack (PSTC-5) | 9 piw |
| Shear Resistance (PSTC-7) | |
| 1" × 1" × 2 lbs. @ 90° F. | 100+ hours |
| ½" × ½" × 2 lbs. @ 90° F. | 5 hours |
| SAFT: | 69° C./156° F. |

[1] (C) denotes Cohesive Split

Opening 68 constitutes a stoma inlet portal. It may be noted that the curb 46 is adapted to be received in the opening 68 so that the curb 46 acts as a convenient locator when the ring 70 is applied to the surface 48. It may also be noted that the combined thickness of the adhesive layer 72, the ring 70, and the sidewall of the bag 14 are less than the axial extent of the curb 46, in order to provide a reduced profile for the assembly.

As may be seen in FIG. 5, the bag 14 may be applied to or removed from the mounting member 12 by grasping a tab 74 on the mounting plate 40 and a tab 76 on the ring 70. It may be noted that the tab 76 is provided with an opening 78, as is an identical diametrically opposed tab (not shown), so that a mounting belt (not shown) may be attached thereto for additional security.

Figure 3:
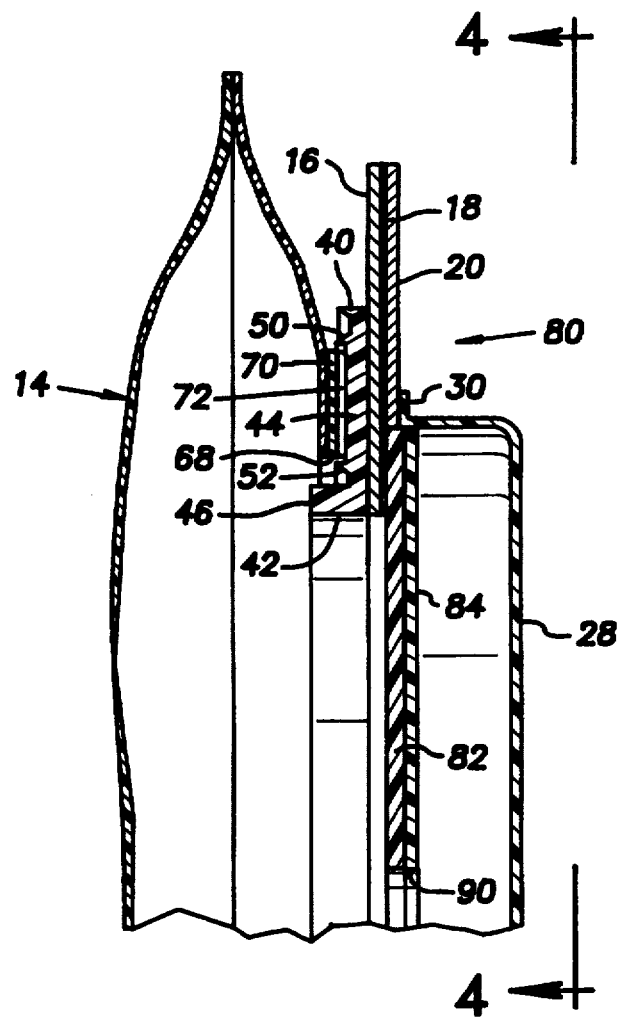
FIG. 3 is a cross-sectional view similar to FIG. 2, but showing a modified aspect of this invention.
Figure 4:
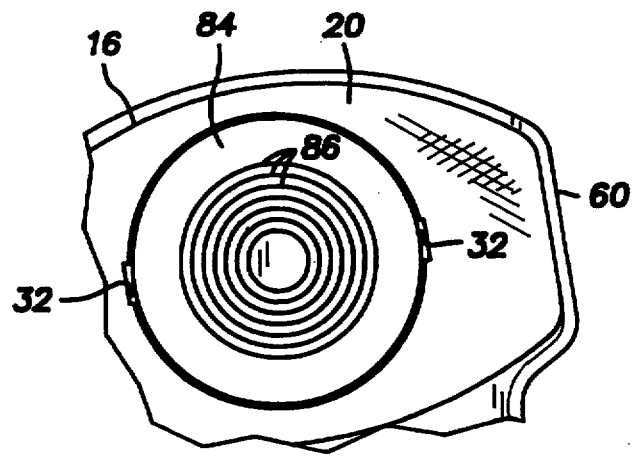
FIG. 4 is a fragmentary, proximal elevational view, the plane of the view being indicated by the line 4—4 in FIG. 3.

Referring now to FIGS. 3 and 4, there is illustrated an ostomy appliance assembly 80 which is similar to the arrangement shown in FIGS. 1, 2, and 5 and, therefore, is identified by identical reference numbers for identical parts. The assembly 80, however, includes a flat annular rim or flange 82 for applications wherein the convex disc 22 is not needed. Here, the flat, annular rim 82 is like the flat, annular rim portion 24 of the embodiment shown in FIG. 2, except that it is a larger flat flange area. The flat annular rim 82 is covered by an adhesive skin barrier 84 which has a number of concentric circles 86 printed or embossed thereon. The rim 82 is preferably made of the same EVA copolymer described above for the convex disc 22, the most preferred EVA copolymer being "Elvax ®". The stoma opening may be tailored to receive a particular size stoma by cutting the skin barrier along a selected concentric indicator. It should be appreciated that such an indicator also may be employed with the embodiment illustrated in FIGS. 1, 2, and 5.

The following example is provided wherein the adhesive used in the invention for releasably attaching the pouch to the mounting plate was tested to determine retention of adhesion after multiple uses. The tests evaluated the rebonding performance of the most preferred pressure-sensitive adhesive 72 described above, after multiple applications and removals of the device, as in actual use by as ostomate. The mounting plate 40 and the mounting ring 70 used in these tests were made of the most preferred ethylene vinyl acetate copolymers as described above. Thus, the tests were conducted on the most preferred embodiment of the invention as a whole.

The peel adhesion was tested by measuring the force needed to peel the pouch away from the mounting plate 40. The pouch mounting ring 70 was peeled away from the plate 40 at an angle of 90° and a speed of 12 inches per minute. The test technique involved mounting the proximal adhesive 18 of plate 12 to an aluminum panel that was of sufficient size to support the entire plate 12. After mounting the plate 12 to the aluminum panel, the actual pouch adhesive 72 was laminated, to the mounting plate 40 and allowed to reside for 30 minutes in one series and 24 hours in a second series at room temperature. Lamination was done using a standard PSTC 4.5 lb. roller. These residence times were selected to indicate, first, initial adhesion and, second, ultimate adhesion of the adhesive to the mounting plate 40. The values obtained with these residence times would serve as base line adhesion values against which rebond values would be compared.

After delamination, the adhesive 72 was rebonded to the same mounting plate 40 and allowed to reside for 30 minutes. Rebonding was done using the same standard PSTC 4.5 lb. roller, and performed as in the original bonding. After 30 minutes of residence, the samples were again peeled at the 90° angle. This cycle was repeated for a total of 5 rebonds after the 30 minute peel test and 2 rebonds after the 24 hour peel test.

In order to check the effect of water which might be used to clean the adhesive surface between uses, the adhesive 72 was wiped with a damp tissue after the peel test. A 10 minute residence time was allowed between wiping and rebonding. The rebonding was accomplished with the PSTC 4.5 lb. roller, and performed as in the original bonding. The adhesive 72 was allowed to reside on mounting plate 40 for 30 minutes prior to peeling.

The re-bonding performance of the pressure-sensitive adhesive 72 was tested in the manner described, and the results presented in the following table were obtained.

| PEEL ADHESION | (Grams) |
| --- | --- |
| 30 Min. Residence (after Attachment) | 857.5 |
| Rebond #1 | 692.6 |
| Rebond #2 | 779.9 |
| Rebond #3 | 961.7 Sl. T.[1] |
| Rebond #4 | 964.6 Sl. T,L.[2] |
| Rebond #5 | 1027 Sl. T,L.[2] |
| 24 Hour Residence | 1171.3 |
| Rebond #1 | 815.1 |
| Rebond #2 | 815.5 |
| Water Wipe - 10 min. dry time | 957.5 |
| Rebond | 997.3 |

[1]Sl.T. = slight transfer of adhesive from ring to plate (approx. 1%)
[2]Sl.T.L. = slight transfer of adhesive with some delamination (localized loss of all adhesive, from ring to plate)
All tests were performed at 72° ± 2° F., and 50 ± 10% relative humidity.

Three samples were used in each test, with the average of the test results reported.

Peel adhesion tests indicated that there was no great effect on the adhesion of the pouch adhesive after debonding and rebonding. The rebonds were performed in succession, with minimal time between them.

Based on these test results, it is demonstrated that no significant change in adhesion after five successive rebonds to the mounting plate flange portion 44. Adhesive transfer and legging were limited to amounts of 5% or less when the adhesive-bearing ring 70 was peeled away from the mounting plate 40. There was no significant change in peel adhesion after the adhesive was wiped with water and allowed to dry to 10 minutes. Thus, the presently disclosed combination of the most preferred ethylene-vinyl acetate copolymers used for the flange 44 and mounting plate 70 and the most preferred pressure-sensitive adhesive used to releasably attach the flange 44 to the plate 70 provides surprisingly and significantly improved efficiency of the ostomy pouch, since it can be cleaned and reused numerous times.

In another series of tests of the ostomy device 10 of the present invention, the vertical load-bearing strength of the releasable adhesive connection between flange 44 and plate 70 was assessed. In actual use, the stress on the bond will be a combination of peel and shear. The drain port 64 on the device 10 was sealed and water was added to fill the device to a level of approximately ⅔ full. This was considered to be a reasonable maximum quantity and weight of collected material, before the bag would be emptied, in normal use. When filled to this level, the bag contains 300 grams of water. A simulation was employed to evaluate the performance of the adhesive under these more realistic conditions, as follows.

The mounting adhesive 18 coated on the surface of the mounting plate member 12 was used to mount the member 12 to a steel panel. The functional pouch adhesive 72 was used to mount the pouch 14 by mounting ring 70 to the mounting plate 40. The PSTC 4.5 lb. roller was used to make the lamination. After a residence time of 30 minutes at room temperature, the panel with the device 10 was mounted vertically and a 500 gram weight was attached to the bottom of the drain 64. The 500 gram weight was used to accelerate the test. The time was noted for any failure of the adhesive. This test, referred to as the Dead Load Shear test, was performed with three samples. After 48 hours, the test was discontinued without the mounting ring 70 separating from the panel in any of the three test samples.

Although the preferred embodiment of this invention has been shown and described, it should be understood that various modifications and rearrangements of the parts may be resorted to without departing from the scope of the invention as disclosed and claimed herein.

What is claimed is:

1. An ostomy appliance having a mounting member adapted to be secured to the periostomal skin surfaces of an ostomate, comprising
   a relatively rigid mounting plate having a centrally located aperture therethrough, said mounting plate defining a flat annular flange portion radially extending from said aperture,
   an adhesive skin barrier on a proximal side of the mounting plate and defining a stoma-receiving opening,
   adhesive web means on a proximal face of said flange portion securely bonded to said proximal face of said flange portion and adapted to adhesively secure said plate to the periostomal skin surfaces of an ostomate, said adhesive web means comprising a breathable material, said breathable material being at least partially covered with a hypo-allergenic adhesive,
   an ostomy pouch formed of a plastic film and having means defining a stoma inlet portal therein, and adhesive means surrounding said inlet portal for removably adhering said pouch to a distal face of said flange portion, said distal face comprising said flange portion having annular curb means projecting axially from said flange portion in a distal direction, said adhesive means comprises a coating of pressure sensitive adhesive applied to a mounting ring surrounding and defining said portal, said mounting ring being adapted to be releasably received and attached to said flange portion, said pressure sensitive adhesive allowing repeated removal and reattachment of the pouch without substantial loss of adhesion or sealing capability of said adhesive, and
   a convex disc peripherally secured to said mounting plate, said adhesive skin barrier being on a proximal face of said disc, said skin barrier and a centrally located port in said disc defining portion of said stoma-receiving opening, said disc consisting essentially of a copolymer of ethylene and vinyl acetate, said copolymer having a vinyl acetate content in the range from 9 to 40 percent, and a melt index in the range from 0.3 to 50 deg/min.

2. An ostomy appliance according to claim 1, wherein said disc contains said vinyl acetate content in the range from 15 to 20 percent and said melt index is in the range from 5 to 15 deg/min.

3. An ostomy appliance according to claim 1, wherein said disc contains said vinyl acetate content of approximately 18 percent and said melt index is approximately 8 deg/min.

4. An ostomy appliance according to claim 3, wherein said pressure-sensitive adhesive is a synthetic formulation based on a formulated styrene-butadiene rubber solution, having a high tack and a high peel adhesion and being capable of forming destructible bonds.

5. An ostomy appliance according to claim 1, wherein an outside diameter of said annular curb means is slightly less than the diameter of said portal so that said curb means is positionable within said portal.

6. An ostomy appliance according to claim 5, wherein the degree of axial projection of said curb means substantially corresponds to the combined thickness of said band of pressure sensitive adhesive and said mounting ring so that a distal face of said curb means is substantially coplanar with a distal face of the mounting ring.

7. An ostomy appliance according to claim 1, wherein said pressure-sensitive adhesive is a synthetic formulation based on a formulated styrene-butadiene rubber solution, having a high tack and a high peel adhesion and being capable of forming destructible bonds.

8. An ostomy appliance having a mounting member adapted to be secured to the periostomal skin surfaces of an ostomate, comprising
   a relatively rigid mounting plate having a centrally located aperture therethrough, said mounting plate defining a flat annular flange portion radially extending from said aperture,
   an adhesive skin barrier on a proximal side of the mounting plate and defining a stoma-receiving opening,
   adhesive web means on a proximal face of said flange portion securely bonded to said proximal face of said flange portion and adapted to adhesively secure said plate to the periostomal skin surfaces of an ostomate,
   an ostomy pouch formed of a plastic film and having means defining a stoma inlet portal therein, said plastic film consisting essentially of a three layer co-extruded barrier film, and adhesive means surrounding said inlet portal for removably adhering said pouch to a distal face of said flange portion, said distal face comprising said flange portion having annular curb means projecting axially from said flange portion in a distal direction, said adhesive means comprises a coating of pressure sensitive adhesive applied to a mounting ring surrounding and defining said portal, said mounting ring being adapted to be releasably received and attached to said flange portion, said pressure sensitive adhesive allowing repeated removal and reattachment of the pouch without substantial loss of adhesion or sealing capability of said adhesive.

9. An ostomy appliance according to claim 8, wherein said barrier film has two outer layers comprising a copolymer of ethylene vinyl acetate, and an inner layer comprising a vinylidene polymer plastic.

10. An ostomy appliance according to claim 9, wherein said pressure-sensitive adhesive is a synthetic formulation based on a formulated styrene-butadiene rubber solution, having a high tack and a high peel adhesion and being capable of forming destructible bonds.

11. An ostomy appliance having a mounting member adapted to be secured to the periostomal skin surfaces of an ostomate, comprising
   a relatively rigid mounting plate having a centrally located aperture therethrough, said mounting plate defining a flat annular flange portion radially extending from said aperture,
   an adhesive skin barrier on a proximal side of the mounting plate and defining a stoma-receiving opening,
   adhesive web means on a proximal face of said flange portion securely bonded to said proximal face of said flange portion and adapted to adhesively secure said plate to the periostomal skin surfaces of an ostomate,
   an ostomy pouch formed of a three layer coextruded barrier film and having means defining a stoma inlet portal therein, and adhesive means surrounding said inlet portal for removably adhering said pouch to a distal face of said flange portion, said distal face comprising said flange portion having annular curb means projecting axially from said flange portion in a distal direction, said adhesive means comprises a coating of pressure sensitive adhesive applied to a mounting ring surrounding and defining said portal, said mounting ring being adapted to be releasably received and attached to said flange portion, said pressure sensitive adhesive allowing repeated removal and reattachment of the pouch without substantial loss of adhesion or sealing capability of said adhesive, said pressure sensitive adhesive comprises a synthetic, formulated styrene-butadiene rubber solution having high tack and high peel adhesion and being capable of forming destructible bonds, and said flange portion consists essentially of a copolymer of ethylene vinyl acetate having a vinyl acetate content of 18 percent and a melt index of 8 degrees per minute, and said barrier film consists essentially of two outer layers comprising a copolymer of ethylene vinyl acetate, and an inner layer comprising a vinylidene polymer plastic.

12. An ostomy appliance having a mounting member adapted to be secured to the periostomal skin surfaces of an ostomate, comprising
   a relatively rigid mounting plate having a centrally located aperture therethrough, said mounting plate defining a flat annular flange portion radially extending from said aperture,
   an adhesive skin barrier on a proximal side of the mounting plate and defining a stoma-receiving opening,
   adhesive web means on a proximal face of said flange portion securely bonded to said proximal face of said flange portion and adapted to adhesively secure said plate to the periostomal skin surfaces of an ostomate,
   an ostomy pouch formed of a plastic film and having means defining a stoma inlet portal therein, said plastic film consisting essentially of a three layer co-extruded barrier film, and adhesive means surrounding said inlet portal for removably adhering said pouch to a distal face of said flange portion, said distal face comprising said flange portion having annular curb means projecting axially from said flange portion in a distal direction, said adhesive means comprises a coating of pressure sensitive adhesive applied to a mounting ring surrounding and defining said portal, said mounting ring being adapted to be releasably received and attached to said flange portion, said pressure sensitive adhesive allowing repeated removal and reattachment of the pouch without substantial loss of adhesion or sealing capability of said adhesive, said pressure sensitive adhesive comprising a synthetic formulation based on a formulated styrene-butadiene rubber solution, having a high tack and high peel adhesion and being capable of forming destructible bonds.

* * * * *